US00PP21811P2

(12) United States Plant Patent
van den Aardwegh

(10) Patent No.: US PP21,811 P2
(45) Date of Patent: Mar. 22, 2011

(54) ***ECHINACEA* PLANT NAMED 'AMBER MIST'**

(50) Latin Name: *Echinacea hybrida*
Varietal Denomination: Amber Mist

(76) Inventor: Cornelis Marinus van den Aardwegh, Hillegom (NL)

( * ) Notice: Subject to any disclaimer, the term of this patent is extended or adjusted under 35 U.S.C. 154(b) by 0 days.

(21) Appl. No.: 12/592,652

(22) Filed: Dec. 1, 2009

(51) Int. Cl.
*A01H 5/00* (2006.01)

(52) U.S. Cl. ..... Plt./428

(58) Field of Classification Search ..... Plt./263, Plt./428

See application file for complete search history.

*Primary Examiner*—Susan B McCormick Ewoldt
(74) *Attorney, Agent, or Firm*—Audrey Charles

(57) ABSTRACT

A new and distinct cultivar of *Echinacea* plant named 'Amber Mist', particularly distinguished by yellow-orange colored ray florets, floriferous, compact habit, healthy, abundant foliage, and good mildew resistance, is disclosed.

1 Drawing Sheet

Latin name of genus and species of plant claimed: *Echinacea hybrida.*

Variety denomination: 'Amber Mist'.

BACKGROUND OF THE INVENTION

The present invention relates to a new and distinct cultivar of *Echinacea* plant botanically known as *Echinacea hybrida* and hereinafter referred to by the cultivar name 'Amber Mist'. The new cultivar originated from an open pollination in 2005 in a nursery location in Hillegom, The Netherlands between unknown male and female *Echinacea* plants. The nursery location was densely populated with *Echinacea purpurea, Echinacea paradoxa* and *Echinacea* hybrids.

The new cultivar was selected from the results of the open pollination in 2007 in Hillegom, The Netherlands. Asexual reproduction of the new *Echinacea* by in vitro propagation in a controlled environment in Hillegom, The Netherlands since the summer of 2008, has shown that the unique features of the *Echinacea* are stable and reproduced true to type in successive generations.

SUMMARY OF THE INVENTION

The following are the most outstanding and distinguishing characteristics of this new cultivar when grown under normal horticultural practices in Hillegom, The Netherlands:

1. Yellow-orange colored ray florets;
2. Floriferous;
3. Compact habit;
4. Healthy, abundant foliage; and
5. Good mildew resistance.

Of the many commercially available *Echinacea* cultivars, the most similar in comparison to the new cultivar is 'Matthew Saul', U.S. Plant Pat. No. 17,652. However, in side by side comparisons in Hillegom, The Netherlands, plants of the new cultivar 'Amber Mist' differ from plants of 'Matthew Saul' in at least the following characteristics:

1. Plants of the new cultivar are more floriferous than plants of 'Matthew Saul';
2. Plants of the new cultivar have a foliage color different from plants of 'Matthew Saul';
3. Plants of the new cultivar have a ray floret color different from plants of 'Matthew Saul'; and 4. Plants of the new cultivar have longer ray florets than plants of 'Matthew Saul'

In addition, plants of the new cultivar 'Amber Mist' are similar to 'Pink Mist', pending U.S. Plant patent application No. 12/592,634. However, in side by side comparisons in Hillegom, The Netherlands, plants of the new cultivar 'Amber Mist' differ from plants of 'Pink Mist' in flower color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Amber Mist'. The plant was field grown for approximately 1 year in Hillegom, The Netherlands in an outdoor nursery location. Plants were transplanted into a one-gallon container for photography purposes.

DETAILED BOTANICAL DESCRIPTION

Figure 1:
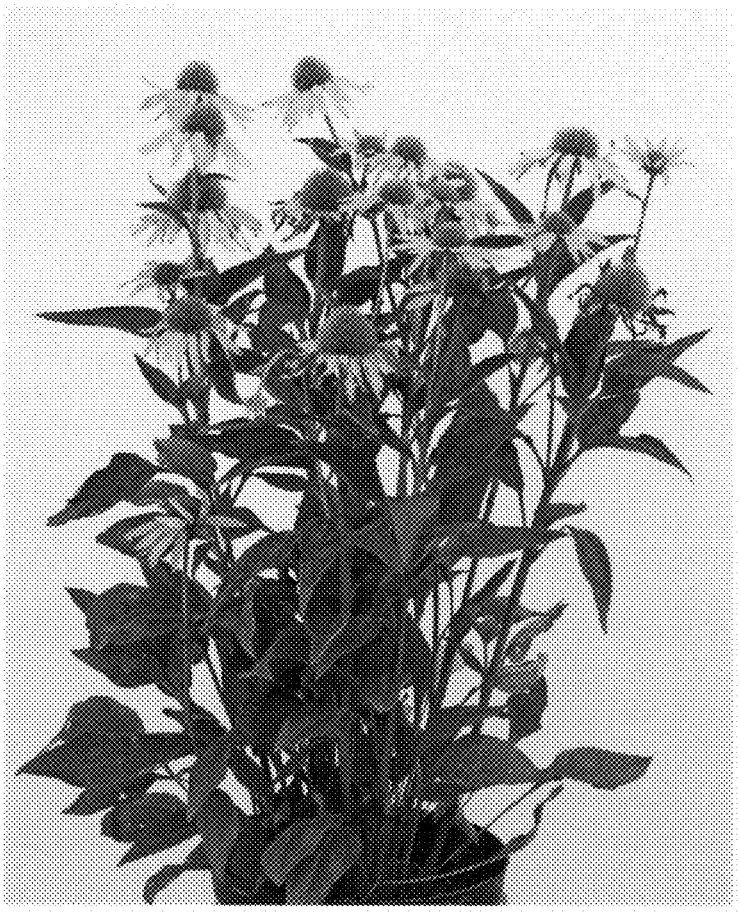
FIG. 1 illustrates a side view of the overall growth and flowering habit of 'Amber Mist'.
Figure 2:
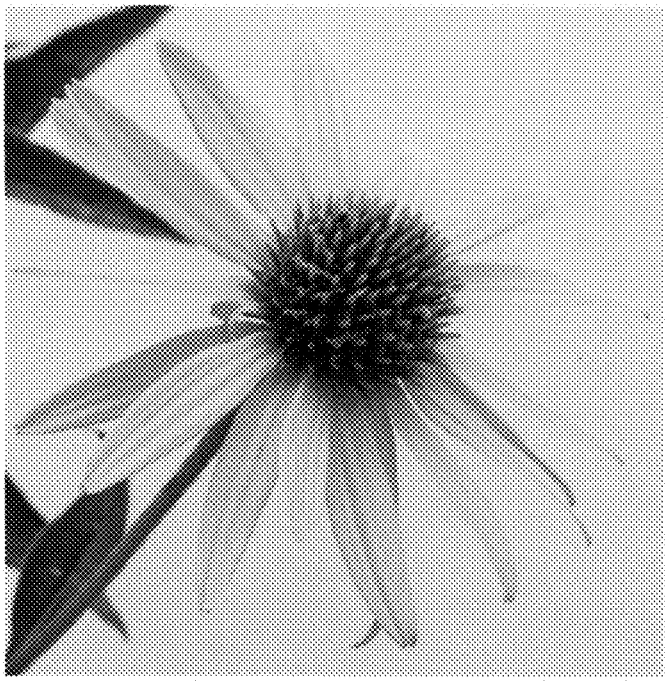
FIG. 2 illustrates a close-up view of an individual inflorescence of 'Amber Mist'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The data which define these characteristics were collected from asexual reproductions carried out in Hillegom, The Netherlands. The plant history was taken in August 2009 on 1-year-old field grown plants which were planted and grown outdoors in daytime temperatures between 14° C. and 28° C. and nighttime temperatures between 5° C. and 18° C. No pinching, growth retardants or photoperiodic treatments were used. Observations were made when the plants were in natural daylight conditions.

Botanical classification: *Echinacea hybrida* cultivar 'Amber Mist'.

Parentage:

*Female parent.*—Unknown *Echinacea* sp.

*Male parent.*—Unknown *Echinacea* sp.

Propagation:

*Type.*—In vitro propagation is preferred, divisions are possible.

*Time to initiate roots in vitro.*—Approximately 30 days at 14° C.

*Time to produce a rooted plantlet in summer.*—Approximately 30 days at 14° C.

*Root description.*—Fine, fibrous; grey in color.

*Rooting habit.*—Moderate density, poorly branched.

Plant description:

*Commercial crop time.*—Approximately 20 weeks from a rooted tissue culture plantlet to finish in a 1 gallon container.

*Growth habit and general appearance.*—Upright, herbaceous perennial.

*Growth rate.*—Moderately vigorous, approximately 17 cm per month in spring.

*Outdoor plant performance.*—Use as bedding plants or in mixed-container plantings; at least tolerant to temperatures up to 35° C. and hardy to USDA zone 4.

*Size.*—Height from soil level to top of plant plane: Approximately 52.3 cm. Width: Approximately 35.8 cm.

*Branching habit.*—No lateral branching, flowering stems grow from base. Quantity of main stems per plant: Approximately 10.

*Stems.*—Strength: Very strong. Aspect: Nearly erect, 5° angle from vertical. Shape: Rounded. Length to base of inflorescence: Approximately 39.7 cm. Diameter: Approximately 5.0 mm. Length of central internode: Approximately 3.6 cm. Texture: Moderately pubescent with short strigose hairs. Length of pubescence: Approximately 0.5 mm. Color of pubescence: 157D. Color of young and mature stems: 144A to 144B.

Foliage description:

*General description.*—Form: Simple. Arrangement: Alternate.

*Leaves.*—Aspect: Acute angle to stem becoming perpendicular and subtending with age. Shape: Narrowly ovate, slightly carinate. Margin: Entire, very slightly undulate. Apex: Acute to long acute. Base: Attenuate. Venation pattern: Pinnate. Length of mature leaf: Approximately 9.6 cm. Width of mature leaf: Approximately 4.2 cm. Texture of upper and lower surfaces: Slightly glossy, moderately to densely pubescent with short strigose hairs. Length of pubescence: Approximately 0.3 mm. Color of pubescence: 157D. Color of upper surface of young foliage: 137A to 137B with venation of 144B. Color of lower surface of young foliage: 143A with venation of 144B. Color of upper surface of mature foliage: 137A with venation of 144B. Color of lower surface of mature foliage: 137C with venation of 144B.

*Petiole.*—Shape: V-shaped. Length: Approximately 9.7 cm. Diameter: Approximately 2.0 mm. Height: Approximately 2.0 mm. Texture: Glabrous. Color: 144B.

Flowering description:

*Flowering habit.*—'Amber Mist' continuously flowers from early July to mid-September in The Netherlands.

*Lastingness of individual inflorescence on the plant.*—Approximately 14 days.

Inflorescence description:

*General description.*—Type: Solitary, composite. Persistent. Shape: Conical. Aspect: Facing upward. Arrangement: Terminal, held upright on strong peduncles. Fragrance: Faintly sweet. Quantity per plant: Approximately 30. Height: Approximately 5.1 cm. Diameter: Approximately 7.5 cm.

*Peduncle.*—Strength: Strong. Aspect: Erect. Length of terminal peduncle: Approximately 6.9 cm. Length of fourth peduncle: Approximately 8.2 cm. Diameter: Approximately 3.0 mm. Texture: Moderately pubescent with short strigose hairs. Length of pubescence: Approximately 0.5 mm. Color of pubescence: 157D. Color: 144A to 144B.

*Bud.*—Quantity per plant: Approximately 10. Shape: Flattened globular with immature ray florets nearly erect. Length: Approximately 1.9 cm. Diameter: Approximately 2.2 cm. Color: 162A to 162B with a center of 143A.

*Ray florets.*—Quantity per inflorescence: Approximately 24. Arrangement: Slightly imbricate in a single whorl. Aspect: Initially at acute angle to disc, becoming perpendicular at maturity and subtending with age. Shape: Lanceolate to narrowly elliptic. Appearance: Dull. Margin: Entire. Apex: Emarginate to praemorse. Base: Cuneate. Length: Approximately 3.5 cm. Width: Approximately 7.0 mm. Texture of upper surface: Smooth, slightly ribbed longitudinally. Texture of lower surface: Smooth, ribbed longitudinally. Color of upper surface when first open: 23A. Color of lower surface when first open: 19B to 19C. Color of upper surface when fully open: 21B fades to 16A to 16B with age. Color of lower surface when fully open: 14D.

*Disc florets.*—Disc diameter: Approximately 3.1 cm. Quantity per inflorescence: Approximately 280. Arrangement: Spirally arranged in center of inflorescence. Shape: Tubular. Margin of free portion: Entire. Apex: Five acute tips. Base: Fused into a tube. Length: Approximately 1.1 cm. Diameter: Approximately 2.0 mm. Texture: Glabrous. Color of upper and lower surfaces when first and fully open: 144A.

*Receptacle.*—Shape: Conical. Height: Approximately 1.1 cm. Diameter: Approximately 9.0 mm. Color: 158D.

*Phyllaries.*—Quantity per inflorescence Approximately 48. Arrangement: In a three whorls. Appearance: Dull, stiff. Shape: Narrowly ovate to lanceolate, slightly curved towards the peduncle. Margin: Entire. Apex: Acute. Base: Cuneate. Length: Approximately 1.0 cm. Width: Approximately 3.0 mm. Texture of upper or inner surface: Glabrous. Texture of lower or outer surface: Glabrous with margins moderately to densely pubescent with short strigose hairs. Length of pubescence: Approximately 0.3 mm. Color of pubescence: 157D. Color of upper and lower surfaces: 138B to 138C.

*Receptacle spines.*—Number of spines per disc: 280. Shape: Acicular. Apex: Acute. Base: Attenuate. Texture: Glabrous. Color: Apex of N25A to N25B with mid-section of 143B and base of 144D.

*Reproductive organs.*—Androecium: Present on disc florets only. Stamen quantity: 5 per floret. Anther shape: Oblong, basifixed. Anther length: Approximately 3.0 mm. Anther color: 200A to 202A. Filament length: Approximately 2.0 mm. Filament color: 145C. Pollen amount: Moderate to abundant. Pollen color: 17A. Gynoecium: Present on disc florets only. Pistil quantity: 1 per floret. Pistil length: Approximately 6.0 mm. Stigma shape: Decurrent. Stigma color: 151B to 151C. Style length: Approximately 5.0 mm. Style color: 151B to 151C. Ovary color: 145C to 145D.

Seed and fruit production: Neither seed nor fruit production has been observed.

Disease and pest resistance: Good mildew resistance. No particular resistance or susceptibility to other diseases or insects noted to date.

What is claimed is:

1. A new and distinct cultivar of *Echinacea* plant named 'Amber Mist', substantially as herein shown and described.

* * * * *